United States Patent [19]
Kushibiki et al.

[11] Patent Number: 5,824,443
[45] Date of Patent: *Oct. 20, 1998

[54] METHOD OF MANUFACTURING SILILCON-TYPE CHARGE TRANSPORTING MATERIALS

[75] Inventors: Nobuo Kushibiki; Kikuko Takeuchi, both of Kanagawa, Japan

[73] Assignee: Dow Corning Asia, Ltd., Tokyo, Japan

[ * ] Notice: The term of this patent shall not extend beyond the expiration date of Pat. No. 5,688,961.

[21] Appl. No.: 743,265

[22] Filed: Nov. 4, 1996

[30] Foreign Application Priority Data

Nov. 6, 1995 [JP] Japan .................................. 7-287634

[51] Int. Cl.$^6$ ................................ G03G 5/00; G03G 5/14
[52] U.S. Cl. ................................ 430/59; 430/73; 430/76
[58] Field of Search ................................ 524/86; 528/38, 528/32; 430/59, 73, 76

[56] References Cited

U.S. PATENT DOCUMENTS

| | | | |
|---|---|---|---|
| 4,752,549 | 6/1988 | Otsuka et al. | 430/58 |
| 5,272,029 | 12/1993 | Sakai et al. | 430/58 |
| 5,436,099 | 7/1995 | Schank et al. | 430/59 |
| 5,688,961 | 11/1997 | Kushibiki et al. | 430/59 |

FOREIGN PATENT DOCUMENTS

| | | |
|---|---|---|
| 55-095953 | 7/1980 | Japan . |
| 238062 | 9/1986 | Japan . |
| 4346356 | 12/1992 | Japan . |

*Primary Examiner*—Tae Yoon
*Attorney, Agent, or Firm*—James L. DeCesare

[57] ABSTRACT

A method of manufacturing solvent-soluble charge transporting materials capable of imparting charge-tranporting properties to polysiloxane resins. These materials have the formula $A\text{-}[R^1SiR^2_{3-n}Q_n]_p$ where A is a tertiary amine and organic group derived from a compound having charge transporting properties with an ionization potential of 4.5–6.2 eV; $R^1$ is an alkylene group of 1–18 carbon atoms; $R^2$ is a monovalent hydrocarbon group or a monovalent halogen-substituted hydrocarbon group of 1–15 carbon atoms; Q is a hydrolyzable group such as—$OR^3$ where $R^3$ is an alkyl group of 1–6 carbon atoms; n and p are each 1–3. This silicon-type charge transporting material is characterized by aromatic groups, and alkoxysilyl groups bonded via hydrocarbon groups onto the aromatic rings.

3 Claims, No Drawings

METHOD OF MANUFACTURING SILILCON-TYPE CHARGE TRANSPORTING MATERIALS

BACKGROUND OF THE INVENTION

This invention is directed to new charge transporting substances used in electrophotographic organic photoconductor.

Electrophotographic organic photoconductor utilizing organic photoconductive materials have been attracting attention from the standpoint of productivity, facility of material design, and safety. They have undergone various improvements and are in use. In recent years, the configuration referred to as function-separation type, in which the layer which generates electric charge and the layer which transports electric charge are separated, has been proposed and put to use. An organic photoconductor with this configuration has two layers. One layer is composed of the charge generating substance and an appropriate resin as binding agent. Another layer above this is the charge transporting substance dispersed or dissolved in a binder resin. The layer containing the charge transporting substance often contains a charge transporting material, and a binder which is a thermoplastic resin such as a polycarbonate resin, polyester resin, acrylic resin, and polystyrene resin; or a thermosetting resin such as a polyurethane resin or epoxy resin. In this case, it is necessary to apply a negative charge through a corona discharge device to the surface of the electric charge generating layer. However, this process generates ozone which causes degradation of the resin, reduces sensitivity, and reduces electrostatic chargeability of the resin, which leads to mechanical damage in the subsequent process of development, transfer of an image onto paper, and friction generated during cleaning. The reduction in properties of the organic photoconductor caused by such factors has been a persistent problem.

Various studies have been conducted regarding these problems. For example, various attempts have been made to blend the polysiloxane resin with either a copolymer constituent or another resin, as seen in the use of a thermosetting polysiloxane resin as the charge transporting layer (i.e., Japanese Laid-Open Patent Application Kokai 61-238062); the use of a protective layer containing a polysiloxane resin (i.e., Japanese Laid-open Patent Application Kokai 62-108260); the use of a protective layer of a thermosetting polysiloxane resin in which silica gel, urethane resin, and/or a polytetrafluoroethylenel resin have been dispersed (i.e., Japanese Laid-Open Patent Application Kokai 4-346356); and the use of a thermoplastic resin in which a thermosetting polysiloxane resin has been dispersed as a protective layer or as an electric charge transporting material binder resin (i.e., Japanese Laid-Open Patent Application Kokai 4-273252). Studies have also been made to improve the performance, extend the life, and improve the cleaning property of organic photoconductor by utilizing the properties of a polysiloxane.

Polysiloxane resins possess desirable characteristics such as transparency, ability to withstand dielectric breakdown, photostability, and low surface tension, which are characteristics not seen in other resins. But because they are incompatible with organic compounds, they are not used alone as the resin constituting the charge transporting material. Rather, polysiloxane resins are used to improve the quality of the resin making up the charge transporting material through copolymerization or blending. In order for polysiloxane resins to be used alone as the binder making up the charge transporting layer, it is necessary that charge transporting substance be dissolved in the polysiloxane resin. Thus, the purpose of our invention is to provide a method of manufacturing such a charge transporting material which can be dissolved in the polysiloxane resin, and impart the electric charge transporting property to the resin used in an electrophotographic organic photoconductor.

BRIEF SUMMARY OF THE INVENTION

Our invention relates to a method of manufacturing a silicon-type charge transporting material represented by the formula $A\text{-}[R^1SiR^2{}_{3-n}Q_n]_p$ where A is an aromatic substituted tertiary amine which has a plurality of aromatic groups, and represents an organic group derived from a compound having charge transporting properties with an ionization potential within the range of 4.5 . 6.2 eV; $R^1$ is an alkylene group of 1–18 carbon atoms; $R^2$ is a monovalent hydrocarbon group or a monovalent halogen-substituted hydrocarbon group of 1–15 carbon atoms; Q is a hydrolyzable group; n and p are each integers from 1–3. The silicon-type charge transporting material is characterized in that it represents an aromatic substituted tertiary amine which has a plurality of aromatic groups, a silyl group which is hydrolyzable, and the silyl group is introduced via a hydrocarbon group into an aromatic ring of at least one of the aromatic groups of the compound with the charge transporting properties with the ionization potential of 4.5–6.2 eV. Examples of hydrolyzable group Q include hydroxy, methoxy ethoxy, butoxy, methylethylketo oxime, diethylamino, acetoxy, propenoxy, propoxy, and Cl. Of these groups, the alkoxy group, especially alkoxy groups with 1–6 carbon atoms, is preferable.

DETAILED DESCRIPTION

Silicon-type charge transporting compounds according to our invention have an ionization potential of 4.5–6.2 eV. When the ionization potential is less than 4.5 eV, the silicon-type charge transporting material is easily oxidized and deteriorated making it undesirable. When the ionization potential exceeds 6.2 eV, injection of charge from the charge generating layer is inhibited, resulting in decreased sensitivity making it undesirable. The ionization potential in our invention was measured by open-air photoelectric spectrometry using surface analyzer AC-1 manufactured by Riken Keiki.

In the silicon-type charge transporting material provided by our invention, the organic silicon group is bonded to an electron-donor group via a hydrocarbon group. The reason is that if it is bonded directly, the $\pi$ electron of the aromatic group in the charge transporting material is affected by the $\pi$–d interaction effect with the d electron of silicon; changing the ionization potential from that of the base material. Bonding via a hydrocarbon group prevents this phenomenon and facilitates designing of the organic photoconductor.

One method of introducing a hydrocarbon group between an aromatic ring and a silicon atom is to bond an unsaturated aliphatic group to at least one of multiple aromatic rings in the charge transporting compound, with an alkoxysilane whose essential substituent for the silicon atom is hydrogen and an alkoxy group, by means of a hydrosilylation reaction. For example, the silicon-type charge transporting material may be manufactured by means of a hydrosilylation reaction between a vinyl group substituted onto an aromatic ring bonded to nitrogen of an aromatic substituted tertiary amine whose ionization potential is 4.5–6.2 eV, and an organic silicon compound with a hydrogen bonded to silicon. One method of introducing the vinyl group to the aromatic group is to first formylate the hydrogen or the methyl group on the aromatic ring, then convert the resulted aldehyde group to the vinyl group by the Wittig reaction, thus allowing introduction of the vinyl group. After this process, the hydrosilylation reaction can be employed. Another method would be to bromomethylate a saturated hydrocarbon group such as methyl, which has been substituted onto the aromatic group, producing a lithio-complex, and then reacting this with a halogenated alkoxysilane.

The aromatic substituted tertiary amine A with an ionization potential of 4.5–6.2 eV used in the method of our invention may constitute any of the compounds shown below, where Me is methyl, Et is ethyl, Ph is phenyl, Bu is butyl, and Pr is propyl.

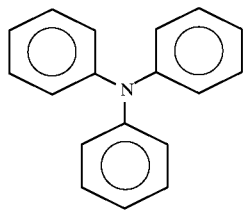

1A

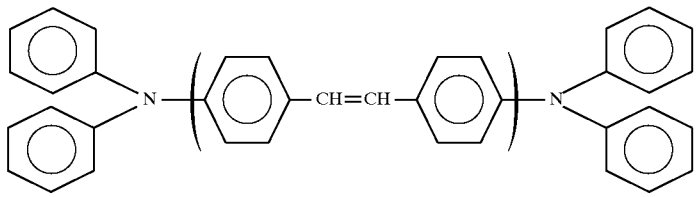

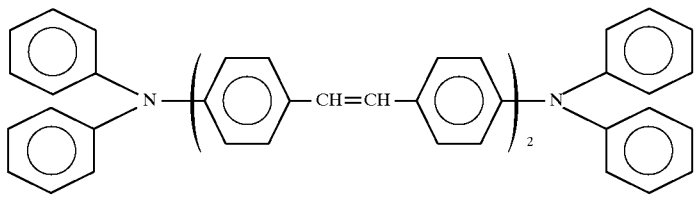

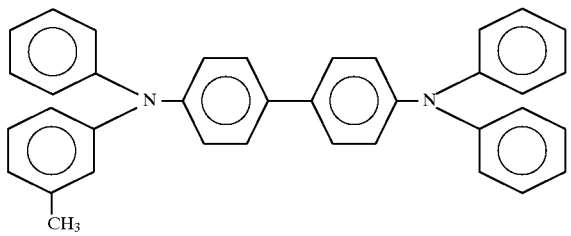

1B

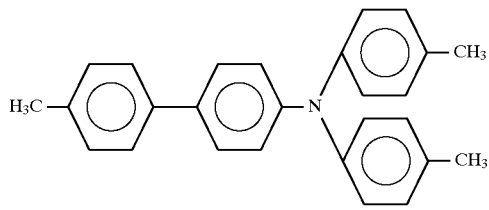

1C

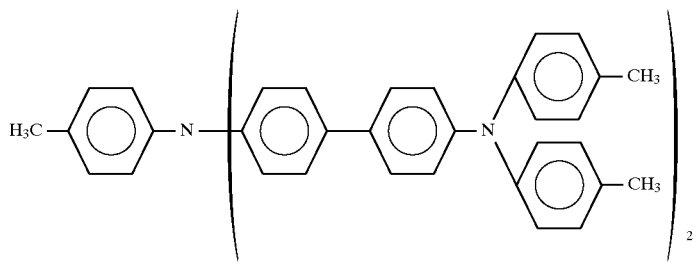

-continued
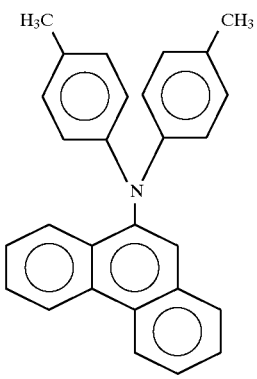
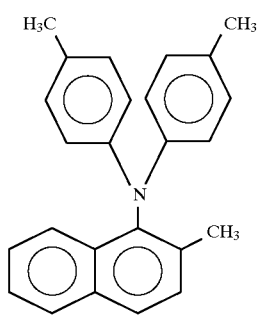
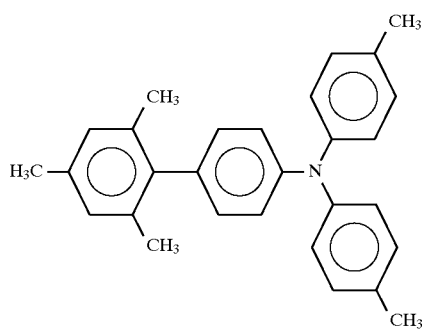
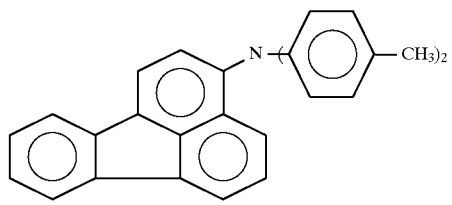
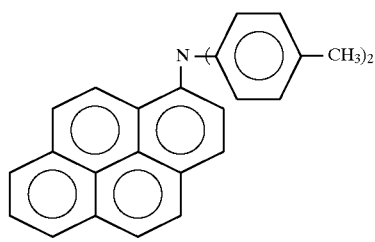

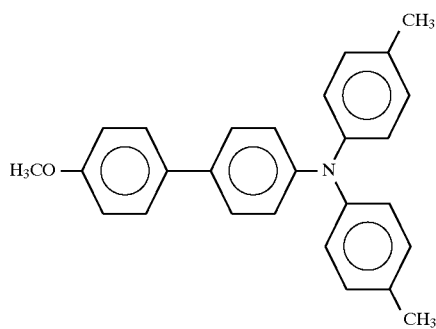
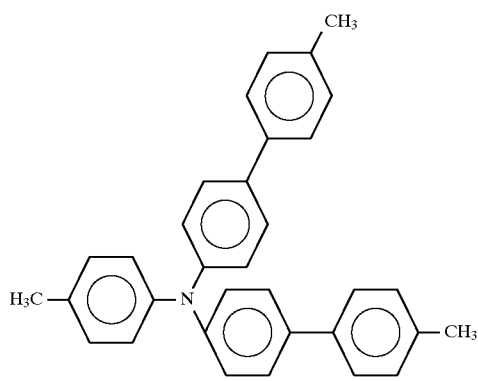
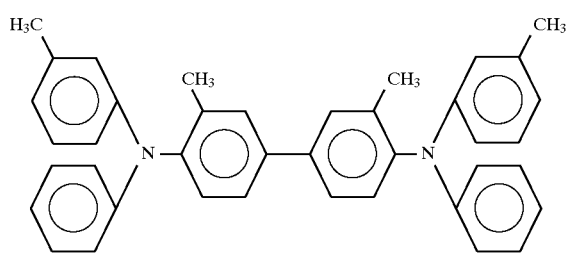
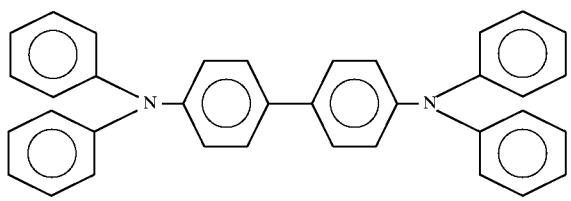
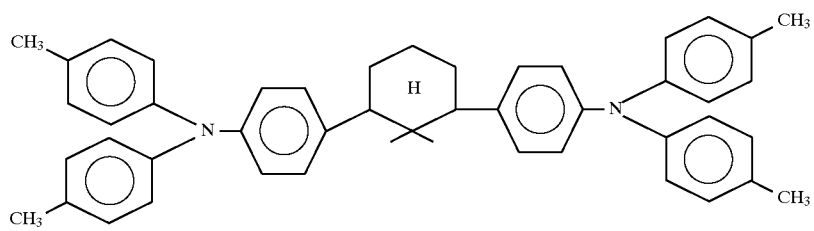
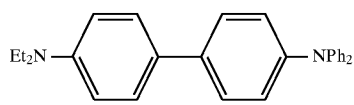

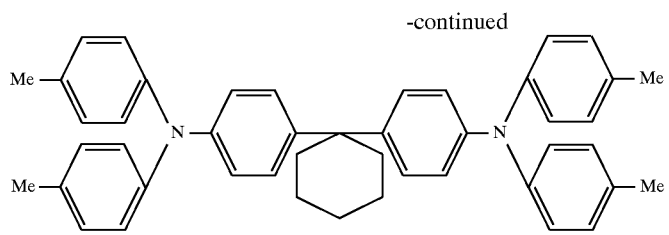
5B
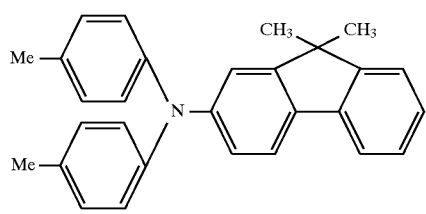
5C
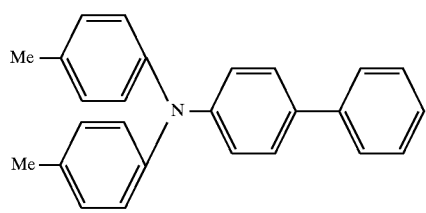
5D
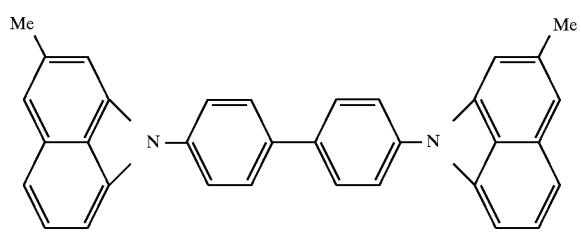
6A
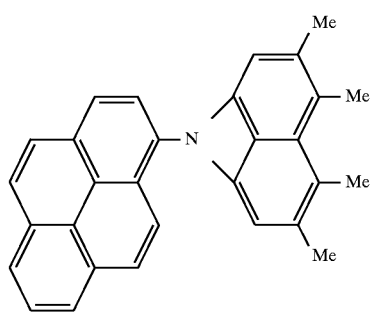
6B
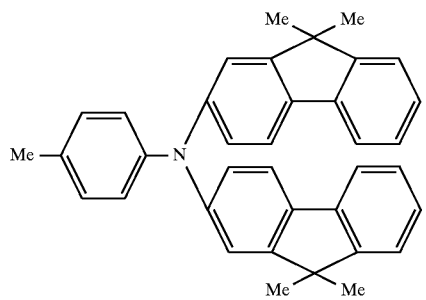
6C
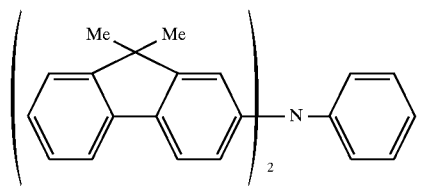
6D

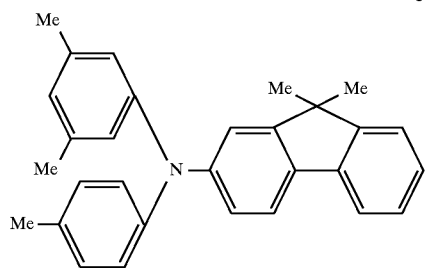
7A
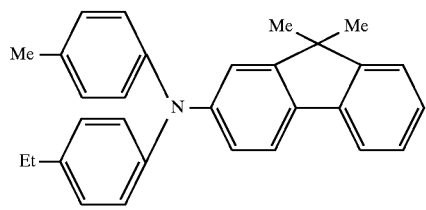
7B
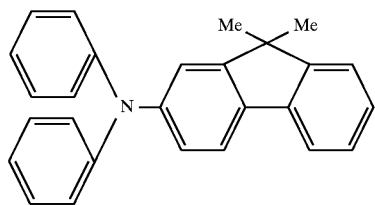
7C
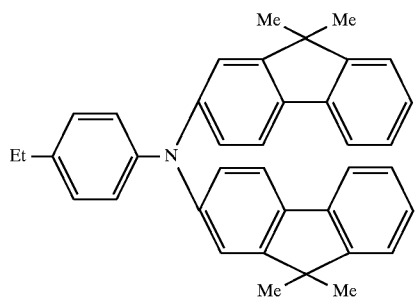
8A
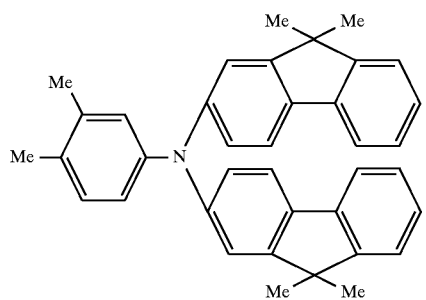
8B
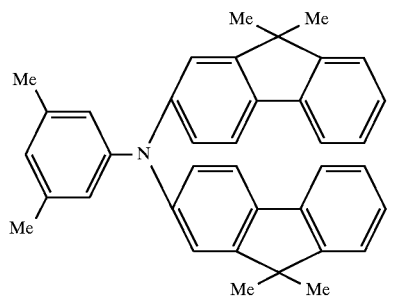
8C -continued
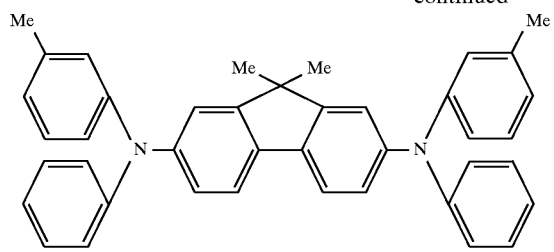
9A
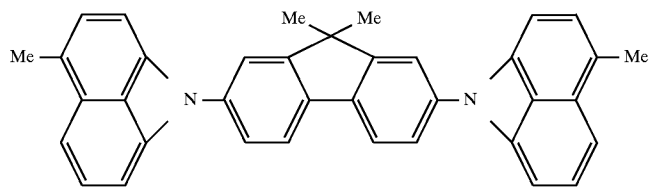
9B
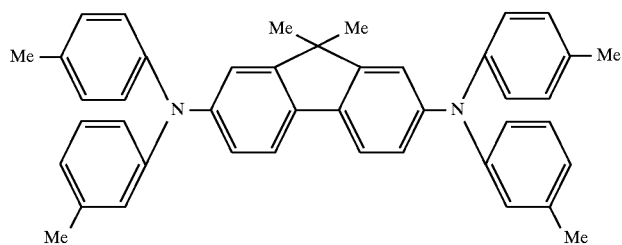
9C
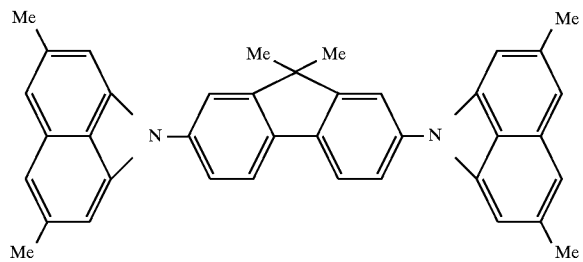
9D
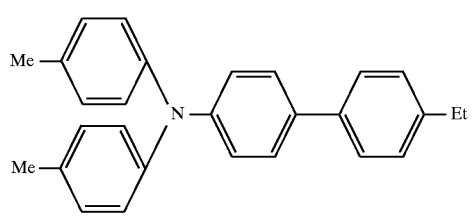
10A
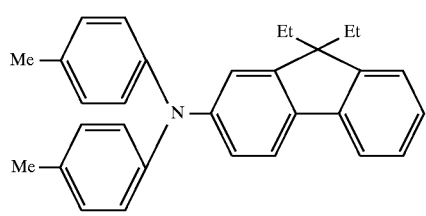
10B
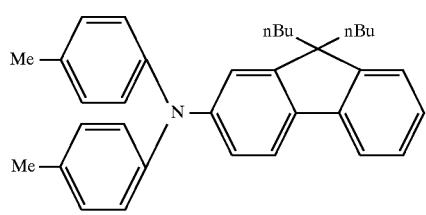
10C -continued
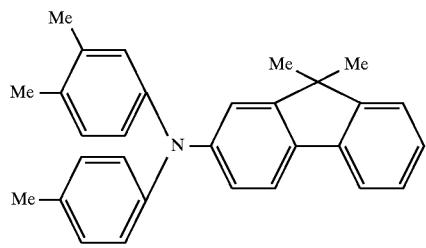
10D
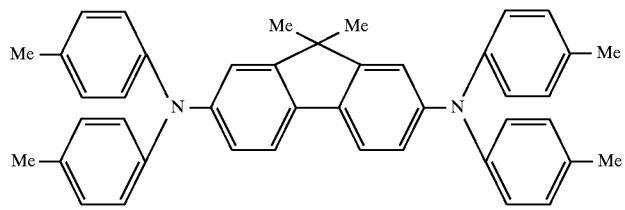
11A
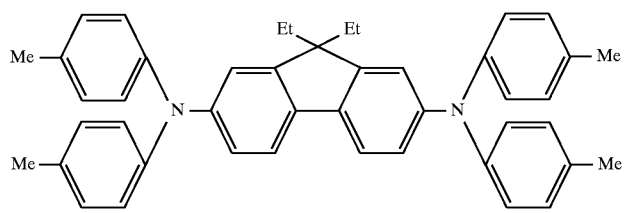
11B
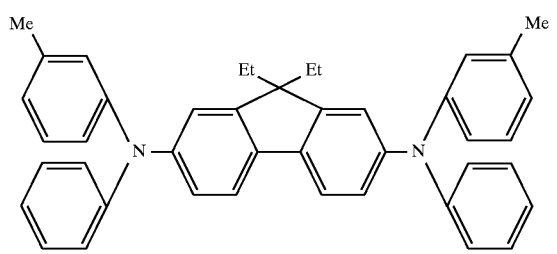
11C
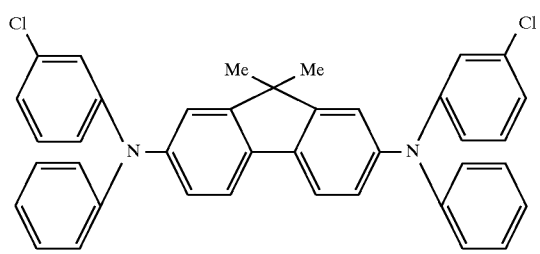
11D
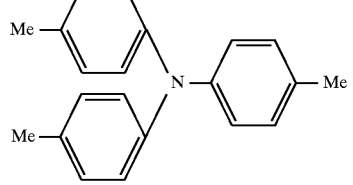
12A
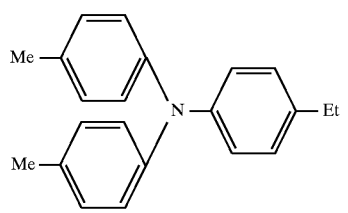
12B -continued
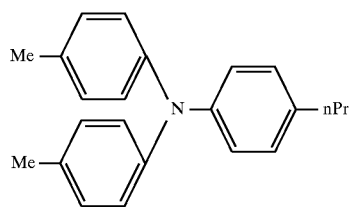
12C
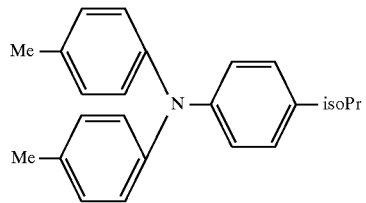
12D
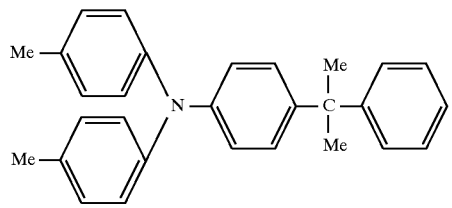
13A
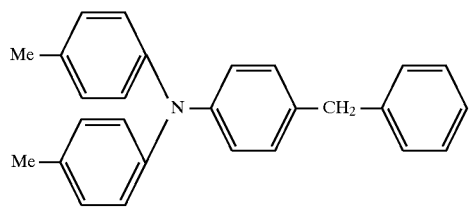
13B
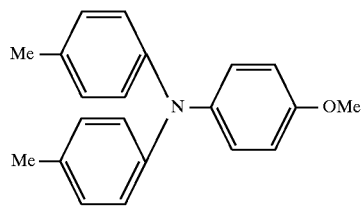
13C
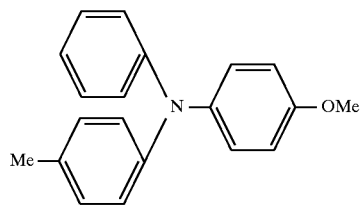
13D
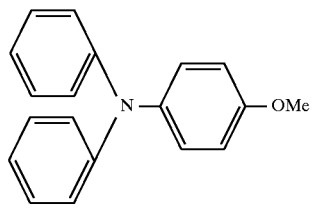
14A -continued
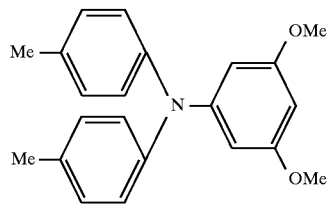
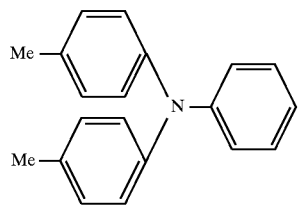
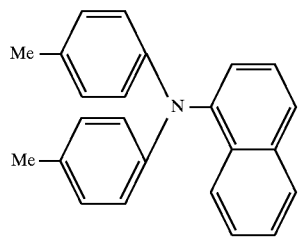
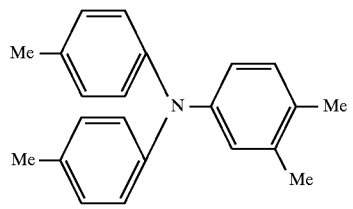
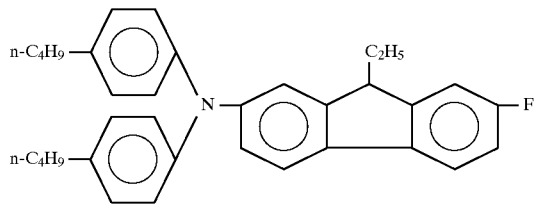
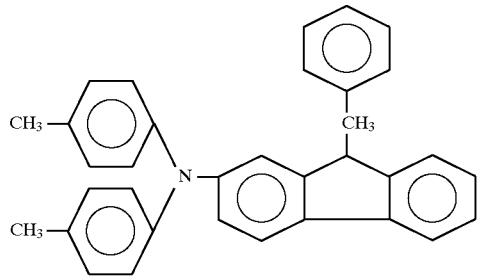
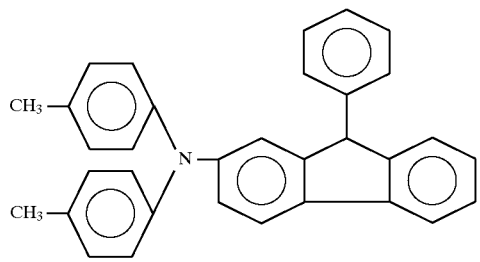
14B
14C
14D
14E -continued
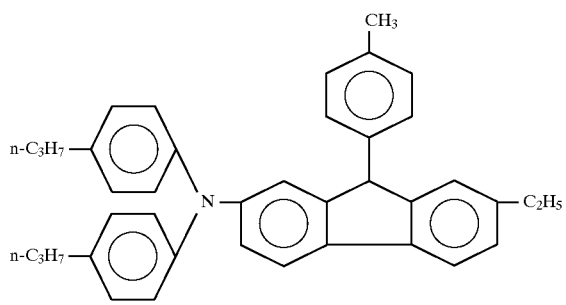
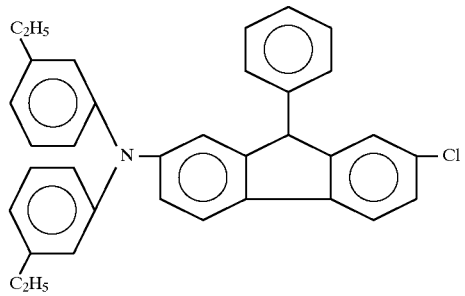
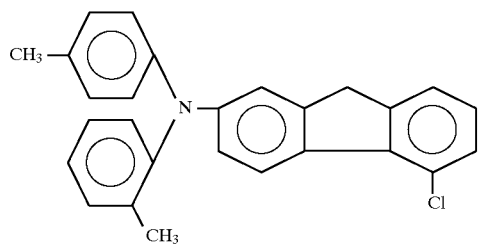
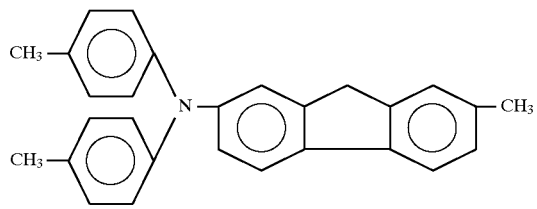
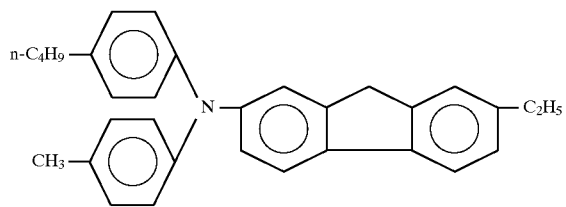
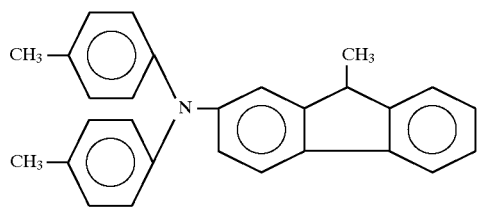

-continued
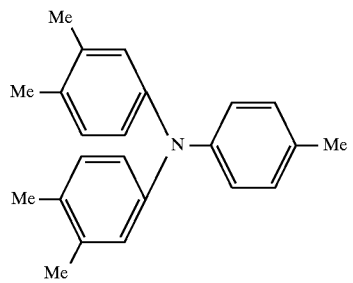
17A
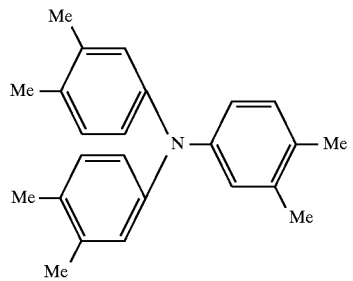
17B
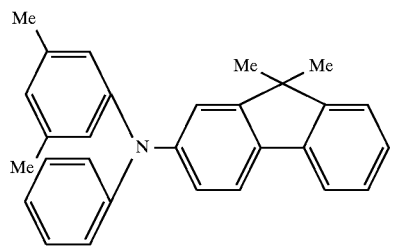
17C
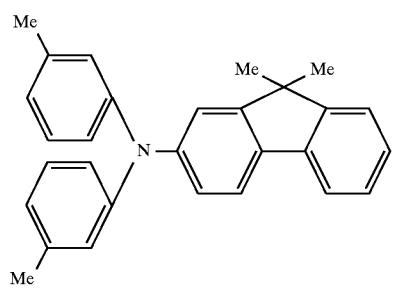
17D
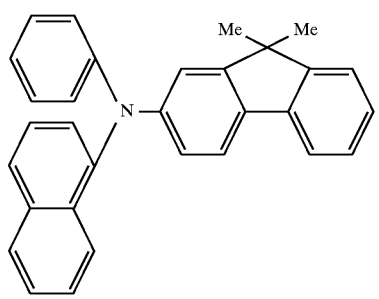
18A
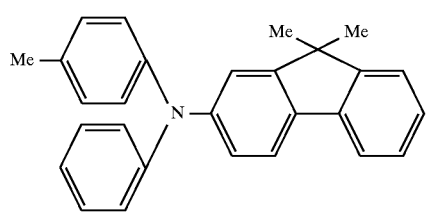
18B -continued

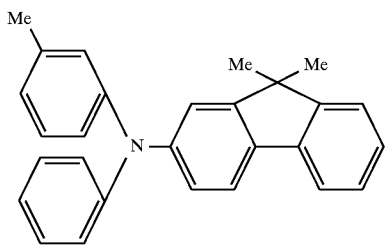

18C

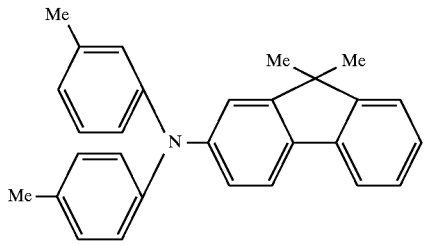

18D

Following are representative ionization and oxidation potentials for some of the aromatic substituted tertiary amines A shown above. These ionization and oxidation potentials refer to the specific compounds identified above with corresponding reference indicia.

1A-Ionization potential: 5.7 eV
1B-Oxidation potential: 0.78 V Ionization potential: 5.42 eV
1C-Oxidation potential: 0.81 V Ionization potential: 5.45 eV
3A-Oxidation potential: 0.84 V Ionization potential: 5.47 eV
5A-Oxidation potential: 0.57 V Ionization potential: 5.22 eV
5B-Oxidation potential: 0.75 V Ionization potential: 5.40 eV
5C-Oxidation potential: 0.76 V Ionization potential: 5.40 eV
5D-Oxidation potential: 0.86 V Ionization potential: 5.49 eV
6A-Oxidation potential: 0.76 V Ionization potential: 5.40 eV
6B-Oxidation potential: 0.79 V Ionization potential: 5.43 eV
6C-Oxidation potential: 0.75 V Ionization potential: 5.40 eV
6D-Oxidation potential: 0.77 V Ionization potential: 5.41 eV
7A-Oxidation potential: 0.80 V Ionization potential: 5.44 eV
7B-Oxidation potential: 0.79 V Ionization potential: 5.43 eV
7C-Oxidation potential: 0.88 V Ionization potential: 5.51 eV
8A-Oxidation potential: 0.76 V Ionization potential: 5.40 eV
8B-Oxidation potential: 0.74 V Ionization potential: 5.38 eV
8C-Oxidation potential: 0.77 V Ionization potential: 5.41 eV
9A-Oxidation potential: 0.63 V Ionization potential: 5.28 eV
9B-Oxidation potential: 0.62 V Ionization potential: 5.27 eV
9C-Oxidation potential: 0.58 V Ionization potential: 5.22 eV
9D-Oxidation potential: 0.59 V Ionization potential: 5.23 eV
10A-Oxidation potential: 0.80 V Ionization potential: 5.44 eV
10B-Oxidation potential: 0.78 V Ionization potential: 5.43 eV
10C-Oxidation potential: 0.78 V Ionization potential: 5.43 eV
10D-Oxidation potential: 0.76 V Ionization potential: 5.41 eV
11A-Oxidation potential: 0.58 V Ionization potential: 5.23 eV
11B-Oxidation potential: 0.58 V Ionization potential: 5.23 eV
11C-Oxidation potential: 0.63 V Ionization potential: 5.28 eV
11D-Oxidation potential: 0.77 V Ionization potential: 5.41 eV
12A-Oxidation potential: 0.83 V Ionization potential: 5.47 eV
12B-Oxidation potential: 0.83 V Ionization potential: 5.47 eV
12C-Oxidation potential: 0.84 V Ionization potential: 5.47 eV
12D-Oxidation potential: 0.83 V Ionization potential: 5.47 eV
13A-Oxidation potential: 0.83 V Ionization potential: 5.47 eV
13B-Oxidation potential: 0.85 V Ionization potential: 5.48 eV
13C-Oxidation potential: 0.74 V Ionization potential: 5.38 eV
13D-Oxidation potential: 0.80 V Ionization potential: 5.44 eV
14A-Oxidation potential: 0.83 V Ionization potential: 5.47 eV
14B-Oxidation potential: 0.84 V Ionization potential: 5.47 eV 14C-Oxidation potential: 0.72 V Ionization potential: 5.36 eV 14D-Oxidation potential: 0.73 V Ionization potential: 5.38 eV 14E-Oxidation potential: 0.81V Ionization potential: 5.45 eV 17A-Oxidation potential: 0.78 V Ionization potential: 5.43 eV 17B-Oxidation potential: 0.76 V Ionization potential: 5.40 eV 17C-Oxidation potential: 0.82 V Ionization potential: 5.46 eV 17D-Oxidation potential: 0.82 V Ionization potential: 5.45 eV 18A-Oxidation potential: 0.89 V Ionization potential: 5.52 eV 18B-Oxidation potential: 0.81 V Ionization potential: 5.45 eV 18C-Oxidation potential: 0.84 V Ionization potential: 5.47 eV 18D-Oxidation potential: 0.79 V Ionization potential: 5.43 eV There is no limitation as to which position on the aromatic ring of the tertiary amine that the alkoxysilane be introduced. Nor is it necessary for alkoxysilane groups to be bonded to all aromatic rings. Such determinations are made by considering factors such as solubility in the polysiloxane resin. In this case, the method of introducing a vinyl group to an aromatic ring bonded to nitrogen is to formylate the hydrogen or the methyl group substituted on the aromatic ring, and then to convert the aldehyde group to the vinyl group by the Wittig reaction; thus allowing the introduction of the vinyl group as described above. It can also be produced by means of the dehydrohalogenation between the hydrogen on the secondary amine and the halogenated aromatic group compound which has been substituted by the vinyl group.

The hydrogenated organic silicon compound which is able to react with the vinyl group bonded to an aromatic ring of tertiary amine A with ionization potential of 4.5–6.2 eV, is a hydrogenated organic silicon compound whose substituent on the silicon atom in its molecule is hydrogen or an alkoxy group. This compound is added to the vinyl group by a hydrosilylation reaction. Hydrogen directly bonded to silicon is an indispensable component of the hydrosilylation reaction to add to the vinyl group. Another indispensable component is a hydrolyzable group, such as an alkoxy group —$OR^3$. $R^3$ of the alkoxy group can be a short chain, i.e., 1–6 carbon atoms, such as methyl, ethyl, propyl, butyl, amyl, and hexyl; or $R^3$ can be a branched alkyl. The selection is made depending on the intended use of the product, stability during hydrosilylation, process and hydrolyzable properties.

Integer n in the formula denotes the number of alkoxy groups substituted on silicon. When n is higher than 1, the hydrophilic property of the compound is improved. When there are several groups that are able to be condensed, the compound also acts as a cross-linking agent, so the selection must be made taking into account the hardness of the resin as a result of cross-linking, as well as its hydrophilic property.

Organic group $R^2$ other than hydrogen and alkoxy which is directly bonded to the silicon atom, may be selected according to the type of substituent on the silicon atom in the polysiloxane resin, and according to the various purposes such as the solubility in the resin, reactivity for the hydrosilylation reaction, and other property adjustments of the polysiloxane resin. $R^2$ may be an alkyl group such as methyl, ethyl, propyl, butyl, amyl, and hexyl; alkenyl such as vinyl and allyl; halogenated hydrocarbon groups; aryl such as phenyl; alkaryl such as tolyl; and fluorohydrocarbon groups represented by trifluoropropyl, heptafluoropentyl, and nonafluorohexyl. If the substituent on silicon in the polysiloxane resin is methyl, the solubility is better if $R^2$ is methyl.

The polysiloxane resin is a resin soluble in organic solvents, and primarily constituting silicon-type macromolecules known as MT resins, MQ resins, T resins, and polysilsesquioxanes. Methods of manufacturing such resins are known, such as the method described on Page 71 of "Silicon-Based Polymer Science", edited by John M. Ziegler and F. W. Gordon Fearon, ACS Series 224, The American Chemical Society (1990).

The hydrosilylation reaction may be conducted using a platinum catalyst or an organic peroxide catalyst. The platinum catalyst can be a platinum compound used in standard hydrosilylation reactions and addition-type silicone rubber; platinum chloride; chloroplatinic acid; platinum-olefin complexes; platinum-phosphine complexes; substances in which platinum is supported by a carrier such as platinum/carbon, platinum/silica gel, and platinum/macromolecules. The quantity of platinum catalyst is that amount used conventionally. In terms of mole ratio, the quantity of platinum metal to alkenyl groups of electron-donor groups should be within the range of 1/100 to 1/100,000. The hydrosilylation reaction temperature varies depending on the type of platinum catalyst used, its quantity, reaction group materials, and reaction conditions. However, from the standpoint of efficiency, it is desirable that the temperature be below the decomposition temperature of the platinum catalyst, i.e., below 200° C. In the case of an organic peroxide catalyst, the only limitation is that its half-life be above room temperature. Organic peroxides which are useful are radical polymerization initiators such as lauryl peroxide, butyl peroxide, and benzoyl peroxide.

Products of hydrosilylation reactions can be divided into two groups. In one group, the silicon atom is added to the alpha position of the vinyl group. In the other group, the silicon atom is added to the beta position of the vinyl group. The position depends on reaction conditions, such as type of vinyl compound substituent and type of catalyst used. In our invention, there is no adverse effect of a mixture of the alpha-additions and beta-additions in the hydrosilylation process. In fact, having a mixture is preferable since it prevents aggregation of electron hole transferring materials which tend to easily form aggregates. The following examples illustrate our invention in more detail.

PRACTICAL EXAMPLE 1

Synthesis of 4-[2-(triethoxysilyl) ethyl] triphenylamine and Synthesis of 4-(N,N-diphenylamino) benzaldehyde 101.4 g of triphenylamine and 35.5 mL of dimethyl formamide (DMF) were placed in a three-neck flask, and while stirring with cooling in ice water, 84.4 mL of phosphorus oxychloride was dropped into the flask. The temperature was raised to 95° C., and the mixture was reacted for 5 hours. The reaction solution was poured into 4 L of warm water and stirred for 1 hour. The precipitate was then collected and washed in a 1:1 mixture solution of ethanol/water, and 4-(N,N-diphenylamino) benzaldehyde was obtained. The yield was 91.5 g (yield rate of 81.0%).

Synthesis of 4-vinyltriphenylamine 14.6 g of sodium hydride and 700 mL of 1,2-dimethoxyethane were placed in a three-neck flask, and while stirring at room temperature, 130.8 g of tetramethylphosphonium bromide was added. After adding one drop of anhydrous ethanol, the mixture was reacted for 4 hours at 70° C. Then 100 g of 4-(N,N-diphenylamino) benzaldehyde was added to the mixture. The temperature was raised to 70° C., and the mixture was reacted for 5 hours. The reaction solution was filtered, and an ether extract of the precipitate and the filtrate were washed in water. Next, the ether solution was dehydrated with calcium chloride, the ether was removed, and the reaction mixture was obtained. This was recrystallized from ethanol, and a needle-form, lemon-yellow vinyltriphenylamine was obtained. The yield was 83.4 g (yield rate of 84.0%).

Hydrosilylation of 4-vinyltriphenylamine 40 mL of toluene, 9.9 g (60 mmol) of triethoxysilane, and 0.018 mmol of a toluene solution of tris-(tetramethyldivinyldisiloxane) diplatinum (0) were placed in a three-neck flask, and while stirring under room temperature, 20 mL of a toluene solution of 8.2 g of 4-vinyltriphenylamine was dropped into the flask. Upon completion of the addition of the drops, the mixture was stirred for 3 hours at 70° C, then the solvent was removed under reduced pressure. As a result, a lemon-yellow oily substance of 4-[2-(triethoxysilyl) ethyl] triphenylamine was obtained. The amount obtained was 12.1 g (yield 91.7%).

PRACTICAL EXAMPLE 2

Synthesis of 4-[2-(methyldiethoxysilyl) ethyl] triphenylamine and Hydrosilylation of 4-vinyltriphenylamine 40 mL of toluene, 8.1 g of methyl diethoxy silane, and 0.018 mmol of a toluene solution of tris-(tetramethyldivinyldisiloxane) diplatinum (0) were placed in a three-neck flask, and while stirring under room temperature, 20 mL of a toluene solution of 8.2 g of 4-vinyltriphenylamine was dropped into the flask. Upon completion of the addition of the drops, the mixture was stirred for 3 hours at 70° C., then the solvent was removed under reduced pressure. As a result, a lemon-yellow oily substance of 4-[2-(methyldiethoxysilyl) ethyl] triphenylamine was obtained. The amount obtained was 11.2 g (yield 91.4%).

PRACTICAL EXAMPLE 3

Synthesis of 4,4', 4"-tris-[2-(triethoxysilyl) ethyl] triphenylamine and Synthesis of tri-(4-formylphenyl) amine 50.7 g of triphenylamine and 53.3 mL of DMF were placed in a three-neck flask, and while stirring while cooling in ice water, 126.6 mL of phosphorus oxychloride was dropped into the flask. Upon completion of the addition of the drops, the mixture solution was reacted for 5 hours at 95° C., then poured into 5 L of warm water, and stirred for 1 hour. The precipitate was then collected by filtering and washed in a 1:1 mixture solution of ethanol/water. As a result, tris-(4-formylphenyl) amine was obtained in an amount of 65.3 g (yield 95.9%).

Synthesis of tri-(4-vinylphenyl) amine 14.6 g of sodium hydride and 700 mL of 1,2-dimethoxy ethane were placed in a three-neck flask, and while stirring at room temperature, 130.8 g of tetramethyl phosphonium bromide was added. Anhydrous ethanol was then added by dripping, and after completion of dripping, a reaction was carried out for 4 hours at 70° C. The reaction mixture was then combined with 40.2 g of tri-(4-formylphenyl) amine, and the reaction was continued for 5 hours at 70° C. The reaction product was filtered. The filtrated cake was extracted with ethanol, and after being combined with the filtrate, was washed with water. After dehydrating the ether solution with calcium chloride, the ether was removed, and a reaction mixture was obtained. This mixture was twice recrystallized with ethanol. As a result, a needle-like lemon-yellow substance of tri-(4-vinylphenyl) amine was obtained. The amount obtained was 38.4 g (yield 97.3%).

Hydrosilylation of tri-(4-vinylphenyl) amine 40 mL of toluene, 9.9 g (60 mmol) of triethoxysilane, and 0.018 mmol of a toluene solution of tris-(tetramethyldivinyldisiloxane) diplatinum (0) were placed in a three-neck flask, and while stirring under room temperature, 20 mL of a toluene solution of 3.3 g (13 mmol) of tri-(4-vinylphenyl) amine was dropped into the flask. Upon completion of the addition of the drops, the mixture was stirred for 3 hours at 70° C., then the solvent was removed under reduced pressure. As a result, a lemon-yellow oily substance of 4,4', 4"-[2-(triethoxysilyl) ethyl] triphenylamine was obtained, and the amount obtained was 7.8 g (yield 80.6%).

PRACTICAL EXAMPLE 4

Synthesis of 4-[N,N-bis-(3,4-dimethylphenyl) amino]-[2-(triethoxysilyl) ethyl] benzene and Synthesis of N,N-bis-(3, 4-dimethylphenyl) aminobenzene 38.5 g (166 mmol) of 4-iodo-o-xylene, 22.9 g (166 mmol) of anhydrous potassium carbonate, and 7.0 g of copper powder were added to 20 mL of nitrobenzene, and heat-refluxed for 8 hours while stirring. The mixture was cooled, filtered, and the filtrate was removed. The obtained reaction mixture was passed through a silica gel column, and N,N-bis-(3,4-dimethylphenyl) aminobenzene was obtained. The amount obtained was 15.7 g (yield rate of 69%).

Synthesis of 4-[N,N-bis-(3,4-dimethylphenyl) amino] benzaldehyde 124.6 g of 4-[N,N-bis-(3,4-dimethylphenyl) amino] benzene and 35.5 mL of DMF were placed in a three-neck flask, and while stirring while cooling in ice water, 84.4 mL of phosphorus oxychloride was dropped into the flask. Upon completion of the addition of the drops, the mixture solution was reacted for 5 hours at 95° C., then poured into 4 L of warm water, and stirred for 1 hour. The precipitate was collected and washed in a 1:1 mixture solution of ethanol/water, and 4-[N,N-bis-(3,4-dimethylphenyl) amino] benzaldehyde was obtained. The amount obtained was 107.6 g (yield rate of 79.0%).

Synthesis of 4-[N,N-bis-(3,4-dimethylphenyl) amino] styrene 12.1 g of sodium hydride and 580 mL of 1,2-dimethoxyethane were placed in a three-neck flask, and while stirring at room temperature, 108.5 g of tetramethyl phosphonium bromide was added. After adding one drop of anhydrous ethanol, the mixture was reacted for 4 hours at 70° C. 100 g of 4-[N,N-bis-(3,4-dimethylphenyl) amino] benzaldehyde was added to the reaction mixture, and the mixture was reacted for 5 hours at 70° C. The reaction solution was filtered, and an ether extract of the filtered cake and filtrate were washed in water. The ether solution was dehydrated with calcium chloride. The ether was removed and the reaction mixture was obtained. This was recrystallized twice with ethanol, and a needle-form of 4-[N,N-bis-(3,4-dimethylphenyl) amino] styrene was obtained. The amount obtained was 84.5 g (yield rate of 85.0%).

Hydrosilylation of 4-[N,N-bis-(3,4-dimethylphenyl) amino] styrene 40 mL of toluene, 6.0 g of triethoxysilane, and 0.54 mmol of a toluene solution of tris-(tetramethyldivinyldisiloxane) diplatinum (0) were placed in a three-neck flask, and while stirring under room temperature, 20 mL of a toluene solution of 9.9 g of 4-[N,N-bis-(3,4-dimethylphenyl) amino] styrene was dropped into the flask. Upon completion of the addition of the drops, the mixture was stirred for 3 hours at 70° C.

The solvent was removed under reduced pressure, and a lemon-yellow oil of 4-[N,N-bis-(3,4-dimethylphenyl) amino]-[2-(triethoxysilyl) ethyl] benzene was obtained. The amount obtained was 13.4 g (yield rate of 90.1%).

PRACTICAL EXAMPLE 5
Synthesis of 4-[N,N-bis-(3,4-dimethylphenyl) amino]-[2-(triethoxysilyl) ethyl] benzene and Hydrosilylation of 4-[N,N-bis-(3,4-dimethylphenyl) amino] styrene 40 mL of toluene, 6.0 g (37 mmol) of triethoxysilane, and 0.34 mmol of dichloro-(n-cycloocta-1,5-diene) platinum were loaded into a three-neck flask. While being stirred at room temperature, 20 mL of a toluene solution of 9.9 g of 4-[N,N-bis-(3,4-dimethylphenyl) amino] styrene was dropped into the flask. Upon completion of the addition of the drops, the mixture was stirred for 3 hours at 70° C. The solvent was removed under reduced pressure, and a lemon-yellow oily substance of 4-[N,N-bis-(3,4-dimethylphenyl) amino]-[2-(triethoxysilyl) ethyl] benzene was obtained. The amount obtained was 14.0 g (yield was 94.2%).

PRACTICAL EXAMPLE 6
Synthesis of 4-[3-(triethoxysilyl) propyl] triphenylamino)-(4-bromotriphenylamine)

8.0 g (45 mmol) of N-bromosuccinimide (NBS) and 10.0 g (41 mmol) of triphenylamine were loaded in a 200 mL three-neck flask and then 150 mL of N,N-dimethyl formamide was added. The components were stirred overnight at room temperature. N,N-dimethyl formamide was removed, and the solid substance obtained was extracted with carbon tetrachloride. Carbon tetrachloride was removed, and the reaction mixture was twice recrystallized with ethanol. As a result, a solid white substance of 4-bromotriphenylamine was obtained in an amount of 8.2 g (yield was 61.7%).
Synthesis of 4-N,N-diphenylamino allylbenzene A 300 mL four-neck flask was filled with 1.0 g (40 mmol) of magnesium metal and the flask was filled with nitrogen. Diethyl ether was added in an amount of 100 mL, and stirring was initiated. 30 mL of a diethyl ether solution of 8.6 g (27 mmol) of 4-bromotriphenylamine was slowly added by dripping into the stirred mixture. After the dropped amount reached 3 mL, refluxing was slowly started. In the course of refluxing, the addition of diethylether solution by dripping was continued. Upon completion of dripping, refluxing was carried out for another hour. A Grignard reagent solution obtained in the manner described above was cooled to room temperature, and combined with 40 mL of a diethylether solution of 2.1 g (27 mmol) of allyl chloride added slowly by dripping. Upon completion of dripping, the reaction mixture was refluxed for 2 hours, and allowed to cool. Ice-cold water was added in an amount of 50 mL, and hydrolysis was carried out. The ether layer was extracted, washed once with an aqueous saturated sodium bicarbonate solution, and twice with water. The product was dried with anhydrous sodium sulfate. After drying, diethylether was removed, and a white solid substance of 4-N,N-diphenylamino allylbenzene was obtained in an amount of 4.9 g (yield 63.2%).
Hydrosilylation of 4-N,N-diphenylamino allylbenzene 40 mL of toluene, 6.0 g (37 mmol) of triethoxysilane, and 0.54 mmol of a toluene solution of tris-(tetramethyldivinyldisiloxane) diplatinum (0) were loaded into a three-neck flask. While being stirred at room temperature, 20 mL of a toluene solution of 9.7 g (34 mmol) of 4-N,N-diphenylamino allylbenzene was dropped into the flask. Upon completion of addition of drops, the mixture was stirred for 3 hours at 70° C. The solvent was removed under reduced pressure, and a lemon-yellow oily substance of 4-[3-(triethoxysilyl) propyl] triphenylamine was obtained. The amount obtained was 10.7 g (yield was 70.1%).

PRACTICAL EXAMPLE 7
Synthesis of 4-[4-(triethoxysilyl) butyl] triphenylamine and Synthesis of 4-methyltriphenylamine 4.5 g (27 mmol) of diphenylamine, 11.0 g (51 mmol) of p-iodotoluene, 5.5 g (40 mmol) of anhydrous potassium carbonate, and 1.1 g of copper chips were added to 30 mL of o-dichlorobenzene. The mixture was subjected to heating and refluxing for 7 hours under stirring conditions. Upon completion of the reaction, the reaction solution was filtered, the filtrate was washed with a 3–5% aqueous solution of sodium thiosulfate, and then with saturated brine. After drying the organic layer with anhydrous sodium sulfate, the solvent was removed. The reaction mixture obtained was recrystallized with ethanol, and 4-methyltriphenylamine was obtained in an amount of 5.7 g (yield 81.4 %).
Synthesis of 4-bromomethyltriphenylamine 6.9 g (39 mmol) of N-bromosuccinimide and 9.1 g (35 mmol) of 4-methyltriphenylamine were loaded in a 300 mL three-neck flask, and 100 mL of carbon tetrachloride was added. The components were stirred overnight. Upon completion of the reaction, the reaction solution was cooled and then filtered. The solvent was removed, The reaction mixture obtained was recrystallized with ethanol. As a result, the substance 4-bromomethyltriphenylamine was obtained in an amount of 10.8 g (yield was 91.2%).
Synthesis of 4-N,N-diphenylamino phenyl-1-butene A 200 mL four-neck flask was filled with 1.0 g (40 mmol) of magnesium metal, and the flask was filled with nitrogen. Diethyl ether was added in an amount of 100 mL, and stirring was initiated. 20 mL of diethyl ether solution of 9.1 g (27 mmol) of 4-bromomethyltriphenylamine was slowly added by dripping to the stirred mixture. After the dropped amount reached 5 mL, refluxing was slowly started. In the course of refluxing, addition of diethylether solution by dripping was continued. Upon completion of dripping, refluxing was carried out for another hour. A Grignard reagent solution obtained in the manner described above was cooled to room temperature, and combined with 20 mL of a diethylether solution of 2.1 g (27 mmol) of allyl chloride which was added slowly by dripping. Upon completion of dripping, the reaction mixture was refluxed for 2 hours, and the reaction was cooled. Ice-cold water was added in an amount of 50 mL, and hydrolysis was carried out. The ether layer was extracted, washed once with an aqueous saturated sodium bicarbonate solution, twice with water. The product was dried with anhydrous sodium sulfate. After drying, diethylether was removed, and a white solid substance of 4-N,N-diphenylamino phenyl-1-butene obtained in an amount of 5.5 g (yield 66.7%).
Hydrosilylation of 4-N,N-diphenylamino phenyl-1-butene 40 mL of toluene, 9.9 g (60 mmol) of triethoxysilane, and 0.018 mmol of a toluene solution of tris-(tetramethyldivinyldisiloxane) diplatinum (0) were placed in a three-neck flask. While stirring under room temperature, 20 mL of a toluene solution of 16.7 g (54.7 mmol) of 4-N,N-diphenylamino phenyl-1-butene was dropped into the flask. Upon completion of addition of the drops, the mixture was stirred for 3 hours at 70° C. The solvent was removed under reduced pressure. As a result, a lemon-yellow oily substance of 4-[4-(triethoxysilyl) butyl] triphenylamine was obtained. The amount obtained was 13.9 g (yield 83.2%).

In view of the above, it can be seen that our invention provides an electron hole transfer material which allows practical application of low surface energy polysiloxane organic photoconductive resins that have excellent hardness and weather resistant properties, unattainable by conventional technique. The silicon-type electron hole transferring material provided by our invention can be used not only in electrophotographic processes, such as photocopiers and laser beam printers, but also as an electric charge transfer layer necessary in construction of organic electroluminescent elements.

Other variations may be made in the compounds, compositions, and methods described herein without departing from the essential features of our invention. The forms of our invention are exemplary and not intended as limitations on its scope as defined in the appended claims.

We claim:

1. A method of manufacturing silicon charge transporting materials A-$[R^1SiR^2_{3-n}Q_n]_p$ where A is a vinyl group containing aromatic substituted tertiary amine with a plurality of aromatic groups; $R^1$ is an alkylene group of 1–18 carbon atoms; $R^2$ is a monovalent hydrocarbon group or a monovalent halogen-substituted hydrocarbon group of 1–15 carbon atoms; Q is a hydrolyzable group; and n and p are each 1–3;

the said method comprising introducing a hydrocarbon group between an aromatic ring of the compound having charge transporting properties which contains a vinyl group substituted onto the aromatic ring, and a silicon atom of an organic silicon compound with a hydrogen atom bonded to silicon, by means of hydrosilylation.

2. The method according to claim 1 wherein hydrolyzable group Q is an alkoxy group.

3. A silicon charge transporting material made according to the method defined in claim 1.

* * * * *